United States Patent [19]

Shroot et al.

[11] Patent Number: 4,654,354
[45] Date of Patent: Mar. 31, 1987

[54] RETINOIC ACID DERIVATIVES, PROCESS FOR THEIR PREPARATION AND PHARMACEUTICAL AND COSMETIC COMPOSITIONS CONTAINING THEM

[75] Inventors: Braham Shroot, Antibes; Gérard Lang, Saint Gratien; Jean Maignan, Tremblay-Les-Gonesse; Michel Colin, Livry-Gargan, all of France

[73] Assignee: Centre International De Recherches Dermatologiques (C.I.R.D.), Valbonne, France

[21] Appl. No.: 780,019

[22] Filed: Sep. 23, 1985

[30] Foreign Application Priority Data

Sep. 26, 1984 [LU] Luxembourg ............................ 85556

[51] Int. Cl.[4] .......................................... C07D 409/00
[52] U.S. Cl. .................................... 514/372; 514/301; 514/373; 514/725; 514/852; 514/859; 514/864; 548/209; 548/213; 546/114
[58] Field of Search ................. 548/209, 213; 514/372, 514/373, 725, 852, 859, 864

[56] References Cited

U.S. PATENT DOCUMENTS

| | | | |
|---|---|---|---|
| 3,562,283 | 2/1971 | Lewis et al. | 548/213 |
| 3,849,430 | 11/1974 | Lewis et al. | 548/213 |
| 3,870,795 | 3/1975 | Miller et al. | 548/213 |
| 4,105,431 | 8/1976 | Lewis et al. | 71/67 |

FOREIGN PATENT DOCUMENTS

| | | |
|---|---|---|
| 3342538 | 5/1984 | Fed. Rep. of Germany . |
| 3092768 | 1/1977 | Japan .................... 548/213 |
| 1113634 | 5/1968 | United Kingdom ................ 548/213 |
| 2087388 | 5/1982 | United Kingdom . |
| 2118554 | 11/1983 | United Kingdom . |
| 2131295 | 6/1984 | United Kingdom . |

OTHER PUBLICATIONS

Experientia, vol. 34, No. 9, Sep. 15, 1978, pp. 1105-1119.

Primary Examiner—Glenna M. Hendricks
Attorney, Agent, or Firm—Cushman, Darby & Cushman

[57] ABSTRACT

The invention provides compounds of formula

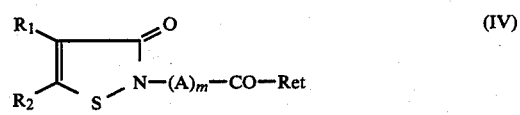

in which formula $R_1$ and $R_2$ are identical or different and denote:
(1) taken separately: a hydrogen atom, a linear or branched $C_1$-$C_4$ alkyl radical, an unsubstituted phenyl radical or a phenyl radical substituted with a halogen atom, with a $C_1$-$C_4$ alkoxy radical or with a $C_1$-$C_4$ alkoxy radical;
(2) taken together either
  (a) a polymethylene linkage; or
  (b) a benzene ring; or
  (c) a cyclic linkage containing a nitrogen atom to constitute an isothiazolopyridinone derivative; m being able to have the values 0 or 1;
the group A in the formula (IV) denoting the group

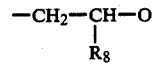

where $R_8$ corresponds to a hydrogen atom, a methyl radical, a hydroxymethyl radical or a —CH$_2$O—CO—Ret group. The invention also provides a process for preparing the abovementioned compounds and also drug compositions and cosmetic compositions containing them.

28 Claims, No Drawings

RETINOIC ACID DERIVATIVES, PROCESS FOR THEIR PREPARATION AND PHARMACEUTICAL AND COSMETIC COMPOSITIONS CONTAINING THEM

This invention relates to novel chemical compounds which are amides or esters of retinoic acid. When the compounds are amides, the nitrogen atom of the amide group is incorporated in an isothiazolone heterocyclic system; when they are esters, the novel compounds are 2-(2'-hydroxy-hydroxyalkyl)isothiazolone retinoates. The invention also relates to a preparative process for obtaining these novel compounds. The invention also relates to the use of these novel compounds, either in cosmetics, or in pharmaceutical preparations in the treatment of dermatological conditions linked to a disorder of keratinisation (differentiation/proliferation) and in the treatment of dermatological or other conditions having an inflammatory and/or immuno-allergic component, and also as pharmaceutical preparations for the ophthalmological field, in particular in the treatment of corneopathies.

The therapeutic action of vitamin A in its acid form (retinoic acid), aldehyde form or alcohol form is well known in dermatology. In this connection see the publication "EXPERIENTIA", volume 34, pages 1105–1119 (1978); this action in the treatment of cutaneous proliferations, acne, psoriasis and similar conditions will be designated hereinafter by the generic expression "retinoid type action". It has been observed that products having a structure similar to vitamin A also show a retinoid type action. The formula of retinoic acid:

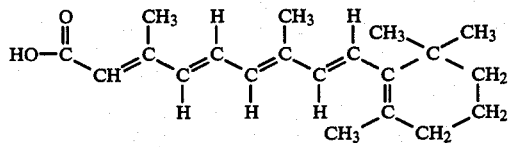

will be denoted in this specification and claims in the abbreviated form:

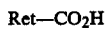     (II)

where only the acid function has been shown explicitly, the remainder of retinoic acid molecule being denoted by "Ret".

It is known that isothiazolones of formula (III)

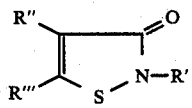     (III)

in which formula R', R" and R''' denote various substituents, have good bactericidal properties; moreover, it is known that a number of these products are highly active on acne germs.

According to the invention, it has been observed that, if the products of formulae (II) and (III) mentioned above are chemically combined, a novel compound is obtained which possesses both the properties of the compounds of formula (II) and those of the compounds of formula (III). However, in addition, it has been observed that the novel compounds thereby obtained have the unexpected property of reducing, or even of eliminating, the irritation due to the use of retinoic acid, in particular in topical application; this surprising property has been demonstrated on tests on rabbits. We have put forward the hypothesis that the novel products according to the invention could, in the treated organism, undergo cleavage giving rise to the compounds of formulae (II) and (III), but that this cleavage, taking place slowly in situ, enables the action of each of the compounds of formulae (II) and (III) to be extended, consequently enabling the irritation caused by the action of retinoic acid to be reduced. This hypothesis is given here although it should be understood this in no way limits the scope of the invention. It is simply one possible explanation of this surprising feature of the novel compounds of the invention.

The present invention hence provides a chemical compound corresponding to the general formula (IV)

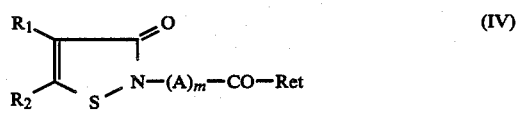     (IV)

in which formula $R_1$ and $R_2$ are identical or different and denote:

(1) taken separately: a hydrogen atom, a linear or branched $C_1$–$C_4$ alkyl radical, an unsubstituted phenyl radical, or a phenyl radical substituted with a halogen atom, with a $C_1$–$C_4$ alkyl radical or with a $C_1$–$C_4$ alkoxy radical;

(2) taken together:
(a) either a polymethylene linkage —$(CH_2)_n$—, n being equal to 3 or 4;
(b) or alternatively a —CH=CH—CH=CH— linkage the benzene ring thus formed being able to be substituted with radicals $R_3$ and $R_4$, which may be identical or different, the radicals $R_3$ and $R_4$ denoting a hydrogen atom, a halogen atom, a $C_1$–$C_4$ alkyl radical, a $C_1$–$C_4$ alkoxy radical, a nitro radical or a carboxyl radical;
(c) or alternatively a linkage of formula (V):

     (V)

in which formula $R_5$, $R_6$ and $R_7$ are identical or different and denote a hydrogen atom or a linear or branched $C_1$–$C_4$ alkyl radical;

m being able to have the values 0 or 1; the group A of the formula (IV) denoting the group

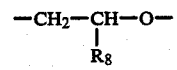

where $R_8$ corresponds to a hydrogen atom, a methyl radical, a hydroxymethyl radical or a $CH_2O$—CO—Ret group.

In the case where $R_1$ and $R_2$ form together a polymethylene linkage, compounds of formula (IV) are derivatives of 4,5-trimethyleneisothiazolone or 4,5-tetra-methyleneisothiazolone.

In the case where $R_1$ and $R_2$ taken together form a benzene ring, the compounds of formula (IV) are benzoisothiazolone derivatives of formula (VII)

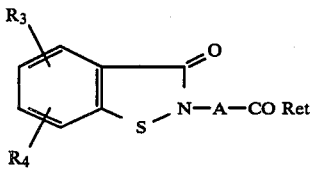 (VII)

$R_3$ and $R_4$ having the significances given above.

In the case where $R_1$ and $R_2$ taken together form a linkage of formula (V), the compounds of formula (IV) are isothiazolopyridinone derivatives corresponding to the formula (VIII)

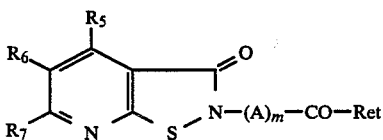 (VIII)

in which $R_5$, $R_6$, $R_7$, A and m have the significances given above.

When m=0, the compounds of formula (IV) are N-retinoylisothiazolones, hence amides of retinoic acid.

When m=1, the compounds of formula (IV) are retinoates, hence esters of retinoic acid, corresponding to the formula (IX)

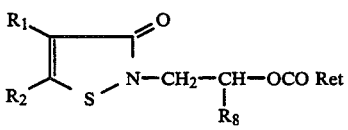 (IX)

in which $R_1$, $R_2$ and $R_8$ have the significances given above.

In the formula (IV), the double bond in the polyene chain α to the carbonyl makes it possible to have two isomeric structures, cis or trans. The invention includes all the geometrical or optical isomers of the compounds of formula (IV).

Among the compounds of formula (IV), the following compounds are preferred:

(1) the compounds for which $R_1$ denotes a hydrogen atom and $R_2$ denotes H, $CH_3$ or $C_6H_5$;

(2) the compound for which $R_1$ and $R_2$ form a polymethylene chain —$(CH_2)_3$—;

(3) the compounds in which $R_1$ and $R_2$ together form an aromatic ring and which are derivatives of benzoisothiazolone or isothiazolopyridinone.

The compounds of formula (IV) can be obtained by reaction of an isothiazolone of formula (X) or (XI)

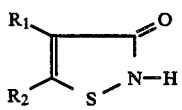 (X)

or

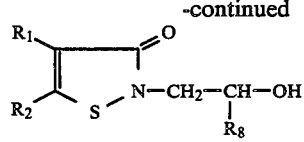 (XI)

with the acid chloride of retinoic acid.

The reactions with the compounds of the formulae (X) or (XI) is typically performed either at room temperature in the presence of approximately 1 equivalent of base in an aromatic solvent such as toluene, or in ether such as tetrahydrofuran, or by bringing a substantially equimolecular toluene solution of retinoyl chloride and isothiazolone to a temperature about 70° C. to 80° C.

When the reaction is performed at room temperature, pyridine or triethylamine can be used as base, and approximately 1 equivalent of retinoyl chloride is then added to the equimolecular isothiazolone/tertiary amine mixture. Sodium hydride can also be used as base. In this case, it is preferred to form the sodium salt of the isothiazolone beforehand, by treating the latter, solubilised in tetrahydrofuran, with approximately 1 equivalent of sodium hydride; when the evolution of hydrogen has ceased, it is considered that all the isothiazolone is converted to its sodium salt; to the latter is then added approximately 1 equivalent of retinoyl chloride.

These reactions should be performed shielded from the moisture in the air and from light. Their progress can be followed by thin layer chromatography (typically on silica gel "F254"). The products obtained can be isolated according to conventional methods. The reaction mixture is washed with water; the organic phase is dried, filtered, concentrated and placed on a silica gel chromatography column; depending on the polarity of the expected product, the latter can be eluted with toluene or methylene chloride. After concentration of the elution phases, the isolated solid can be recrystallised in a toluene/hexane mixture.

The isothiazolones of formula (X) are known products and can be prepared as described in the following:

(a) for some isothiazolones, paper by Sheldon N. Lewis et al., J. Heter. Chem., 1971 p. 571;

(b) for benzoisothiazolones, paper by R. Fischer and H. Hurni, Arzneimittel Forschung, 1964, 14, p. 1301 and paper by Clelland E. W., J. Chem. Soc., 1926, p. 923;

(c) for isothiazolopyridinones, U.S. Pat. No. 3,965,107;

(d) for polymethyleneisothiazolones, French Pat. No. 2,492,376.

The isothiazolones of formula (XI) containing a hydroxyalkyl or dihydroxyalkyl chain in position 2 can be prepared from primary isothiazolones by reacting them with an epoxide such as ethylene oxide, propylene oxide or glycidol.

The retinoyl chloride used in the manufacturing process according to the invention can be prepared according to a conventional method, by reacting phosphorus trichloride with retinoic acid. The two 13-cis and all-trans isomers are commercial products.

According to the invention, it has been observed that the compounds of formula (IV) have a retinoid type action but show only very few irritant features; they are hence especially well suited for treating dermatological conditions linked to a disorder of keratinisation (differentiation/proliferation); it has also been observed that the products of formula (IV) enabled dermatological, or other, conditions having an inflammatory and/or immunoallergic component to be treated. The compounds according to the invention are, in particular, useful for treating acne vulgaris, comedonic or polymorphic acnes, senile acnes, acne solaris, and acne medicamentosa or trade acnes, extended and/or severe forms of psoriasis, and other disorders of keratinisation, in particular ichthyoses and ichthyosiform states, Darier's disease, keratoderma palmaris et plantaris, leukoplakia and leukoplakiform states, lichen planus, and all benign or malignant, severe or extended dermatological proliferations; they are also active in the treatment of rheumatoid psoriasis. Finally, these products find application in the ophthalmological field, in particular for treating corneopathies. The invention hence also relates to drug compositions containing the compounds of formula (IV).

The present invention hence also provides a novel drug composition, intended in particular for treating the abovementioned conditions, characterised in that it contains, in a pharmaceutically acceptable carrier, at least one compound of formula (IV) and/or one of its salts.

When the compounds according to the invention are used topically, they are observed to have high activity over a very large dilution range; in particular, concentrations of active compound(s) ranging from 0.0005% to 2% by weight can generally be used. It is naturally possible to use higher concentrations when this is necessitated for a particular therapeutic application; however, the preferred concentrations of active principle are from 0.002% to 1% by weight. These compositions which can be used topically advantageously take the form of ointments, gels, creams, pomades, powders, dyes, solutions, suspensions, emulsions, lotions, sprays, patches or impregnated pads. The compounds of the invention are mixed with non-toxic inert carriers, generally liquid or pasty, suitable for topical treatment.

The compounds according to the invention can be used enterally. Orally, the compounds according to the invention are suitably administered in the proportion of approximately 2 μg to 2 mg per day per kg of body weight; an excessive dosage can show itself in the form of a vitamin A hypervitaminosis which can be recognised by its symptoms and can lead to fears regarding liver toxicity requiring biological monitoring of hepatic function. The requisite dosage can be administered in one or more doses. For oral administration, the suitable forms are, for example, tablets, gelatin capsules, dragees, syrups, suspensions, emulsions, solutions, powders or granules; a preferred mode of administration consists in using gelatine capsules containing from 0.1 mg to approximately 1 mg of active substance.

The compounds according to the invention can also be administered parenterally in the form of, for example, solutions or suspensions for intravenous or intramuscular perfusion or injection. In this case, compounds according to the invention are administered in the proportion of approximately 2 μm to 2 mg per day per kg of body weight; a preferred mode of administration consists in using solutions or suspensions containing from 0.01 mg to approximately 1 mg of active substance per ml.

When the compounds according to the invention are used for application to the eye, they advantageously take the form of solutions or powders to be diluted for eye lotions.

The pharmaceutically acceptable carrier can comprise water, gelatin, lactose, starch, talc, vaseline, gum arabic, polyalkylene glycols or magnesium stearate. The tablets, powders, dragees, granules or gelatin capsules can contain binders, fillers or pulverulent carriers. The solutions, creams, suspensions, emulsions or syrups can contain diluents, solvents or thickeners.

Compounds of formula (IV) according to the invention also find application in the cosmetic field, especially in body and hair hygiene and, in particular, in the treatment of acne, physiologically dry skin, seborrhoea, hair loss or to promote regrowth of hair. Finally, they have a preventive and curative capacity against the deleterious effects of the sun.

The present invention hence also provides a novel cosmetic composition, characterised in that it contains, in a cosmetically acceptable carrier, at least one compound of formula (IV) and/or one of its salts; this compound can take the form of a lotion, gel, cream, soap, shampoo or the like.

The concentration of compound of formula (IV) in these cosmetic compositions is suitably about 0.0005 to 2% by weight, and preferably 0.01 to 1% by weight, relative to the total weight of the composition.

In the treatment of the abovementioned disorders, the compounds according to the invention, used in the compositions defined above, act by increasing the follicular epithelial production of the non-adherent cells, thereby dislodging and causing the removal of the content of the acne comedo. These compounds reduce the size of the sebaceous glands and partially inhibit the secretion of sebum.

The compounds according to the invention can contain inert or even pharmacodynamically or cosmetically active additives, and in particular:

hydrating agents such as thiamorpholinone and its derivatives or urea, anti-seborrhoeic or anti-acne agents, such as those described in French Pat. Nos. 1,472,021, 1,505,874, 1,560,250, 2,002,461, 2,035,799, 2,011,940, 2,060,407, 2,126,996, 2,133,991, 2,133,992, 2,139,876, 2,158,018, 2,296,406, 2,428,436, 2,468,362, 2,446,277 and 2,447,189, and U.S. Pat. No. 2,332,418, and especially S-carboxymethylcysteine, S-benzylcysteamine, the salts and derivatives thereof, tioxolone or benzoyl peroxide, antibiotics such as erythromycin and its esters, for example those described in U.S. Pat. No. 2,862,921 or French Patent Application No. 85/05785, neomycin, tetracyclines or 4,5-polymethylene-3-isothiazolinones such as are described in French Pat. No. 2,492,376, agents promoting regrowth of hair, such as minoxidil (2,4-diamino-6-piperidinopryimidine 3-oxide) and its derivatives, diazoxide (3-chloromethyl-1,2,4-benzothiadizine, 1,1-dioxide), phenytoin (5,5-diphenyl-2,4-imidazolidinedione), oxapropanium iodide or anthraline and its derivatives, anti-inflammatory agents (steroid and non-steroid), carotenoids, and especially β-carotene, anti-psoriatic agents such as eicosa-5,8,11,14-tetraynoic and -5,8,11-triynoic acids, the esters and amides thereof, anthralin and its derivatives such as those found in French Pat. Nos. 2,113,952, 2,492,372, 2,492,373, 2,495,934 and 2,499,556, or French Patent Application Nos. 84/09203 and 84/10324 or U.S. Pat. No. 4,299,846, and naphthalene and naphthoquinone derivatives such as those described in U.S. Pat. No. 4,229,478, EP No. 7985, or in J.I.D. 84 (4) 358 (1985).

The compositions according to the invention can also contain flavouring agents, preservatives, stabilisers, moisture regulating agents, pH regulating agents, osmotic pressure modifying agents, emulsifiers, UV-A and UV-B filters such as those described in French Pat. Nos. 1,179,387 or 2,528,420 and antioxidants such as α-tocopherol, butylated hydroxyanisole or butylated hydroxytoluene.

To enable the subject of the invention to be more readily understood, several embodiments thereof will now be described. Example A provides the preparation of retinoyl chloride and does not form part of the invention.

EXAMPLE A

Preparation of the acid chloride of all-trans retinoic acid

To a solution of 3 g of all-trans-retinoic acid in 30 cm$^3$ of anhydrous toluene, stirred shielded from the light and from the moisture in the air, 0.3 cm$^3$ of phosphorus trichloride is added dropwise. When the introduction is complete, the mixture is then brought for half an hour to 60° C., after which time all the acid is converted.

This toluene solution is then transferred directly to a dropping funnel for introduction into a solution containing the isothiazolinone.

EXAMPLE 1

Preparation of 2-(all-trans-retinoyl)benzoisothiazolin-3-one

In a three-necked flask equipped with a nitrogen inlet, magnetic stirrer and dropping funnel, a solution of 2.26 g of benzoisothiazolone (0.015 mole) and 1.2 cm$^3$ of pyridine in 75 cm$^3$ of anhydrous toluene is prepared shielded from the light. To this stirred mixture, a crude solution of 0.015 mole of (all-trans) retinoyl chloride is then added dropwise.

A slight exothermic effect is observed and pyridinium chloride precipitates as it is formed. The mixture is stirred for a further 3 hours at room temperature.

It is verified by thin layer chromatography that the starting material is completely converted. The reaction mixture is washed with water until the pH is neutral. The organic phase is then decanted, dried over magnesium sulphate, then concentrated and finally placed on a silica gel chromatography column. The expected product is eluted with toluene.

The solid isolated after evaporation of the elution fractions is crystallised in a toluene/hexane mixture.

1.5 g of orange-yellow crystals melting at 172° C. are obtained.

The $^{13}$C and $^1$H nuclear magnetic resonance spectra correspond to a completely trans structure in the retinoyl chain.

Elementary analysis:

|  | C | H | N | O | S |
|---|---|---|---|---|---|
| Calculated for C$_{27}$H$_{31}$NO$_2$S | 74.79 | 7.21 | 3.23 | 7.38 | 7.39 |
| Found | 74.74 | 7.27 | 3.31 | 7.50 | 7.27 |

EXAMPLE 2

Preparation of 2-(all-trans-retinoyl)-4,5-trimethylene-4-isothiazolin-3-one 0.01 mole (1.41 g) of 4,5-trimethylene-4-isothiazolin-3-one is treated with one equivalent of retinoyl chloride in the presence of pyridine under the same conditions as those described above for benzoisothiazolone.

The expected product is purified by passage on a silica gel column. It is eluted with methylene chloride and recrystallised in a toluene/hexane mixture. 1.5 g of yellow crystals melting at 138° C. are obtained, the $^{13}$C and $^1$H nuclear magnetic resonance spectra of which correspond to a completely trans structure in the retinoyl chain.

The following elementary analysis corresponds to a hydrated product:

|  | C | H | N | O | S |
|---|---|---|---|---|---|
| Calculated for C$_{26}$H$_{33}$NO$_2$S.½ H$_2$O | 72.94 | 7.89 | 3.27 | 8.41 | 7.49 |
| Found | 72.86 | 7.91 | 3.45 | 8.73 | 7.09 |

EXAMPLE 3

Preparation of 2-(all-trans-retinoyl)-4,5-trimethylene-4-isothiazolin-3-one

In a three-necked flask equipped with a nitrogen inlet, magnetic stirrer and dropping funnel, there are placed 5 g of 4,5-(trimethylene)isothiazolin-3-one (0.035 mole) and 350 cm$^3$ of anhydrous tetrahydrofuran. To this prepared solution, 1.2 molar equivalent of sodium hydride is then added. When the formation of the sodium salt of 4,5-(trimethylene)isothiazolin-3-one is complete (cessation of evolution of hydrogen), the solution containing retinoyl chloride (all-trans: 1.2 equivalent) is added dropwise, by means of the funnel, shielded from the light. Two hours after completion of the introduction of the acid chloride, it is verified by thin layer chromatography that the reaction has finished. 3 cm$^3$ of acetic acid are then added to destroy any possible remaining sodium hydride, and the reaction mixture is treated as in the above examples.

After chromatography on a silica gel column and crystallisation, 3 g of 2-(all-trans-retinoyl)-4,5-trimethylene-4-isothiazolin-3-one, also melting at 138° C., are obtained.

EXAMPLE 4

Preparation of 2-(all-trans-retinoyl)isothiazolo[5,4-b]pyridin-3-one

The procedure is as in the case of 4,5-(trimethylene)isothiazolone, initially preparing the sodium salt from 3 g of isothiazolo[5,4-b]pyridin-3-one which is treated with 1.2 equivalent of sodium hydride in 250 cm$^3$ of tetrahydrofuran. When the evolution of hydrogen has ceased, 1.2 equivalent of all-trans-retinoyl chloride, separately prepared, is then added slowly. Stirring is maintained for 3 hours and the reaction medium is left overnight. The following day, it is treated as in the above examples and 2-(all-trans-retinoyl)isothiazolo[5,4-b]pyridin-3-one is purified by chromatography on a silica gel column, followed by crystallisation in a toluene/hexane mixture.

1 g of orange, pearly flakes is obtained, the melting point of which is 198° C.

The mass and nuclear magnetic resonance spectra correspond to the expected structure.

EXAMPLE 5

Preparation of 2-(all-trans-retinoyl)-4,5-tetramethylene-4-isothiazolin-3-one

To a solution of 1 g (0.006 mole) of 4,5-tetramethylene-4-isothiazolin-3-one in 40 cm$^3$ of anhydrous toluene, stirred shielded from the light and from the moisture in the air, one equivalent of retinoyl chloride solubilised in 20 cm$^3$ of toluene is added.

The reaction mixture is then brought for 2 hours to a temperature of 80° C. The majority of the starting material is converted. The toluene is then evaporated off under reduced pressure. The product obtained is solubilised with methylene chloride and the solution is placed on a silica gel column. The 2-(all-trans-retinoyl)-4,5-(tetramethylene)isothiazolone is eluted with methylene chloride. After concentration of the elution phases, the product is recrystallised in a toluene/hexane mixture. 500 mg of orange-yellow crystals melting at 108° C. are obtained.

The mass spectrum (m/e: 437) and the $^1$H 250 MHz nuclear magnetic resonance spectrum corresponds to the expected structure.

EXAMPLE 6

Preparation of 2-(all-trans-retinoyl)-4-isothiazolin-3-one

This product is prepared in the same manner as the derivative described in Example 4. An equimolecular mixture of 1 g of 4-isothiazolin-3-one (0.01 mole) and retinoyl chloride in 60 cm$^3$ of anhydrous toluene is brought to 80° C. for 2 hours. The product is then purified in the same manner as in the above example. 350 mg of orange-yellow crystals melting at 98° C. are obtained.

The mass spectrum (m/e: 383) and the $^1$H 250 MHz nuclear magnetic resonance spectrum correspond to the expected structure.

EXAMPLE 7

Preparation of 2-[2'-(all-trans-retinoyloxy)ethyl]benzoisothiazolone

To a solution of 1.95 g of 2-(2'-hydroxyethyl)bezoisothiazolone (0.01 mole) in 100 cm$^3$ of anhydrous toluene stirred shielded from the light and from the moisture in the air in the presence of 3.6 cm$^3$ of pyridine, one equivalent of all-trans-retinoic acid chloride, solubilised in 50 cm$^3$ of toluene, is added. The mixture is stirred for one hour at room temperature and then for 7 hours at a temperature between 60° and 70° C. The organic phase is washed, and then dried over magnesium sulphate. It is then concentrated under reduced pressure and placed on a silica gel column. The expected product is eluted with methylene chloride. After concentration, 1.5 g of all-trans-retinoate is obtained in the form of a very viscous yellow product.

Elementary analysis:

|  | C | H | N | O | S |
|---|---|---|---|---|---|
| Calculated for C$_{29}$H$_{35}$NO$_3$S | 72.92 | 7.38 | 2.93 | 10.04 | 6.71 |
| Found | 72.72 | 7.42 | 2.97 | 10.11 | 6.71 |

EXAMPLE 8

An anti-seborrhoeic lotion is prepared in the following manner:

To a solution consisting of 10 cm$^3$ of 95° strength ethanol and 30 cm$^3$ of polyethylene glycol (molecular mass: approximately 400) containing 20 mg of butylated hydroxytoluene, 0.1 g of the compound of Example 4 is added.

After solubilisation with agitation, the lotion is applied on the entire head of hair.

A treatment is preferably performed twice daily. After 15 days' treatment, a satisfactory result is observed.

This composition can also be applied on greasy skin.

EXAMPLE 9

The following composition is prepared:

| Compound of Example 2 | 0.1 g |
|---|---|
| Hydroxypropylcellulose sold by HERCULES under the name "KLUCEL HF" | 2.00 g |
| Water/ethanol (50/50) q.s. | 100 g |

A gel is thereby obtained which can be used for treating acne and can be applied one to three times daily, good results are obtained in a period of between 6 and 12 weeks, according to the severity of the case treated.

EXAMPLE 10

The following composition is prepared:

| Compound of Example 7 | 0.5 g |
|---|---|
| Mixture of emulsive lanolin alcohols and refined waxes and oils based on hydrocarbons, sold by B.D.F. MEDICAL under the name "Anhydrous EUCERIN" | 40 g |
| Preservatives q.s. | |
| Sterile demineralixed water q.s. | 100 g |

A nonionic suspension constituting a cream is thereby obtained. This cream, used for treating psoriasis, gives good results in a period of 30 days with one to three applications per day.

EXAMPLE 11

The following composition is prepared:

| Compound of Example 1 | 0.02 g |
|---|---|
| Polyethylene glycol (molecular weight = 400) | 60 g |
| Polyethylene glycol (molecular weight = 4000) | 25 g |
| Liquid paraffin q.s. | 100 g |

An ointment is thereby obtained which can be removed with water. This preparation, used on skin effected by ichthyosis, gives good results.

EXAMPLE 12

The following composition is prepared:

| Compound of Example 7 | 0.001 g |
|---|---|
| Maize starch | 0.150 g |
| Magnesium stearate | 0.250 g |
| Sucrose q.s. | 0.500 g |

A powder is obtained which is packaged in a gelatin capsule composed of gelatin and titanium dioxide.

An adult individual is administered one to three gelatin capsules daily for the treatment of psoriasis, and a significant improvement is observed after approximately 30 days.

We claim:
1. A compound corresponding to the formula (IV):

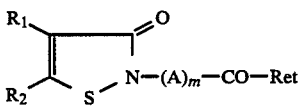

in which formula $R_1$ and $R_1$ are identical or different and denote:
(1) taken separately: a hydrogen atom, a linear or branched $C_1$-$C_4$ alkyl radical, an unsubstituted phenyl radical, or a phenyl radical substituted with a halogen atom, with a $C_1$-$C_4$ alkyl radical or with a $C_1$-$C_4$ alkoxy radical;
(2) taken together: either
 (a) a polymethylene linkage —$(CH_2)_n$—, n being equal to 3 or 4; or
 (b) a —CH=CH—CH=CH— linkage, the benzene ring thus forming being unsubstituted or substituted with radicals $R_3$ and $R_4$, which may be identical or different, the radicals $R_3$ and $R_4$ denoting a hydrogen atom, a halogen atom, a $C_1$-$C_4$ alkyl radical, a $C_1$-$C_4$ alkoxy radical, a nitro radical or a carboxyl radical; or
m is 0 or 1; A denotes the group

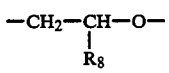

where $R_8$ denotes a hydrogen atom, a methyl radical, a hydroxymethyl radical or a —$CH_2O$—CO—Ret group;
Ret denotes the radical obtained by removing the acid group from retinoic acid or an isomer thereof.

2. A compound according to claim 1, in which $R_1$ denotes a hydrogen atom and $R_2$ is selected from the group consisting of a hydrogen atom and a $CH_3$ or $C_6H_5$ radical.

3. A compound according to claim 1, in which $R_1$ and $R_2$ form a polymethylene chain —$(CH_2)_3$—.

4. A compound according to claim 1, in which $R_1$ and $R_2$ together form an aromatic ring, the said compounds being derivatives of benzoisothiazolone.

5. 2-(all-trans-retinoyl)benzoisothiazolin-3-one.

6. 2-(all-trans-retinoyl)-4,5-trimethylene-4-isothazolin-3-one.

7. 2-[2'-(all-trans-retinoyloxy)ethyl]benzoisothiazolone.

8. A pharmaceutical composition which contains, in a pharmaceutically acceptable carrier, a pharmaceutically effective amount of at least one compound as defined in claim 1.

9. A composition according to claim 8 for treating dermatological conditions linked to a disorder of keratinisation and dermatological, or other, conditions having an inflammatory and/or immuno-allergic component, or for treating rheumatoid psoriasis, or for treating an opthalmic complaint.

10. A composition according to claim 2 for topical application, the concentration of said compound(s) being about 0.0005% to 2% by weight.

11. A composition according to claim 10 in which the concentration of said compound(s) is about 0.01% to 1% by weight.

12. A composition according to claim 10 which is in the form of an ointment, gel, cream, pomade, powder, dye, solution, suspension, emulsion, lotion, spray, patch or impregnated pad.

13. A composition according to claim 8 suitable for enteral use.

14. A composition according to claim 13 for oral use for administration of about 2 μg to 2 mg of said compound(s) per day per kg of body weight.

15. A composition according to claim 14 which is in the form of gelatin capsules containing from about 0.1 mg to about 1 mg of said compound(s) according to one of claims 1 to 4.

16. A composition according to claim 8 which is in the form of a solution or suspension for parenteral administration,.

17. A composition according to claim 16 which is for administration of about 2 μg to 2 mg of said compound(s) per day per kg of body weight.

18. A composition according to claim 16, which contains, per ml of solution or suspension, from about 0.01 of said compound(s).

19. A composition according to claim 8 for administration to the eye.

20. A composition according to claim 8 in which the pharmaceutically acceptable carrier contains at least one product selected from the group consisting of water, gelatin, lactose, starch, talc, liquid petrolatum, gum arabic, a polyalkylene glycol, magnesium stearate, a diluent, a solvent and a thickener.

21. A cosmetic composition which contains, in a cosmetically acceptable carrier, a cosmetically effective amount of at least one compound as defined in claim 1.

22. A composition according to claim 21 for the treatment of acne, physiologically dry skin, seborrhea and hair loss, for the promotion of the re-growth of hair or for the prevention of or protection against the deleterious effects of the sun.

23. A composition according to claim 21 in which the said compound(s) is/are present at a concentration from about 0.0005 to 2% by weight.

24. A composition according to claim 23 in which the said compound(s) is/are present at a concentration from about 0.01 to 1% by weight.

25. A composition according to claim 21 which is in the form of a lotion, gel, cream, soap or shampoo.

26. A composition according to claim 8 which comprises one or more additives selected from the group consisting of hydrating agents, anti-seborrhoeic agents, anti-acne agents, antibiotics, agents promoting the re-growth of hair, anti-inflammatory agents, carotenoids, anti-psoriatic agents, flavouring agents, preservatives, stabilisers, moisture regulating agents, pH regulating agents, osmotic pressure modifying agents, emulsifiers, UV-A and UV-B filters and antioxidants.

27. A composition according to claim 21 which comprises one or more additives selected from the group consisting of hydrating agents, anti-seborrhoeic agents, anti-acne agents, antibiotics, agents promoting the re-growth of hair, anti-inflammatory agents, carotenoids, anti-psoriatic agents, flavouring agents, preservatives, stabilisers, moisture regulating agents, pH regulating agents, osmotic pressure modifying agents, emulsifiers, UV-A and UV-B filters and antioxidants.

28. A method of treating a dermatological condition of a patient which comprises administering to the patient at least one compound as defined in claim 1.

* * * * *